United States Patent [19]

Cheng et al.

[11] Patent Number: 5,304,603
[45] Date of Patent: Apr. 19, 1994

[54] LEYDIG CELL STIMULATOR

[75] Inventors: C. Yan Cheng, Staten Island; C. Wayne Bardin, New York, both of N.Y.

[73] Assignee: The Population Council, New York, N.Y.

[21] Appl. No.: 715,904

[22] Filed: Jun. 18, 1991

[51] Int. Cl.$^5$ ............ A61K 37/00; A61K 37/38
[52] U.S. Cl. .................... 514/12; 514/21; 514/15; 530/397; 530/398; 530/399; 530/416; 530/417; 935/60
[58] Field of Search ............ 514/12, 15, 21; 530/397, 398, 399, 416, 417; 935/60

[56] References Cited

U.S. PATENT DOCUMENTS 5,166,190 11/1992 Mather et al. ............ 514/8

OTHER PUBLICATIONS

"Molecular Cell Biology", J. Darnell, et al., pp. 221-222 and pp. 260-262.
"Protein Purificaiton Methods: A Practical Approach", E. L. V. Harris, S. Angal, eds., pp. 9-10, 57-64.
A. J. W. Hsueh, et al., Proc. Natl. Acad. Sci. USA 84, 5082-5086 (1987).

*Primary Examiner*—Michael G. Witshyn
*Assistant Examiner*—C. Sayala
*Attorney, Agent, or Firm*—Lerner, David, Littenberg, Krumholz & Mentlik

[57] ABSTRACT

The present invention relates to a compound which when administered to Leydig cells in the testes stimulates the production of androgen such as testosterone. This compound, when mixed with other known compounds, can produce testosterone levels in excess of those obtained by the administration of a maximal stimulatory dose of Lutenizing Hormone (LH).

12 Claims, 2 Drawing Sheets

NH2-Val-Ile-Val-Glu-Leu-Xaa-Ala-Ser-Val-

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:1:

Val  Ile  Val  Glu  Leu  Xaa  Ala  Ser  Val
    1                         5

LEYDIG CELL STIMULATOR

FIELD OF INVENTION

The present invention relates to the field of peptides which are useful for the stimulation of androgens, methods for their isolation and production and their use.

BACKGROUND OF THE INVENTION

The testes of male animals including humans, is divided into two function compartments. One compartment which is responsible for the production of sperm, contains a tightly packed series of tubular coils known as the seminiferous tubules. The seminiferous tubules make up the majority of the testes structure. Hormone producing cells located within the seminiferous tubules which assist in the transformation of germ cells to sperm cells are known as Sertoli cells. The other compartment of the testes contains Leydig cells. Leydig cells are responsible for the production of androgens or male sex hormones. These Leydig cells are interspersed between the various coils of the seminiferous tubules.

For years it was known that when a certain chemical bound to specific membrane receptors on Leydig cells, a series of reactions is initiated which result in the production and secretion of androgens. "Androgen" refers to a family of male sex hormones which include, without limitation, dihydrotestosterone, androstenedione and testosterone. Androgens such as testosterone, play a key role in the development of male sexual characteristics such as growth of the penis, muscles and beard as well as deepening of the voice. Testosterone secreted by the Leydig cells was also known to bind to specific receptors in the Sertoli cells and this binding was known to be important in sperm production.

The compound that was known to bind to Leydig cells was Lutenizing Hormone (LH) which is secreted by the pituitary gland under the brain. (A functionally analogous compound produced in females, Chorionic Gonadotropin (CG) or human Chronic Gonadatropin (hCG) can also bind to LH receptors on Leydig cells. CG is easier to obtain than LH and, therefore, clinical studies often use CG instead of LH. Because they are functionally interchangeable, they are often referred to as "LH/CG".) It was originally thought that the binding of LH/CG to the Leydig cell was the sole mechanism for initiating the production of androgens. Another compound, Follicle Stimulating Hormone (FSH) was known to be released by the pituitary gland under the brain and was known to bind to specific membrane receptors on the Sertoli cells. The binding of FSH along with testosterone, to the Sertoli cells were thought to be key to sperm production.

These simplistic explanations of the operation of the Sertoli and Leydig cells were fine for a basic understanding of testicular biology. However, there were certain situations which these explanations just could not accommodate. For example, it was found that when Sertoli cells were damaged, the Leydig cells surrounding them underwent rapid enlargement, without a change in LH levels. This suggests that the life cycle of both types of cells are interdependent, at least to some extent. Furthermore, there is a disease in children that causes the Leydig cells to produce large amounts of testosterone, even in the absence of LH. It has long been believed that some other substance, contained within the testes, activates the Leydig cells to produce androgen in this instance. Finally, in the fetus, testosterone or other androgens are produced before the Leydig cells LH receptors are operational. These observations suggested a symbiotic relationship between the Sertoli cells and the Leydig cells above and beyond their respective known roles in sperm cell production.

The understanding of the chemical interaction between the Sertoli cells and the Leydig cells has gradually grown, particularly over the last ten years. During that period, the results of a number of studies were released and those studies appear to support the symbiotic relationship of Sertoli cells and Leydig cells. For example, when porcine Leydig cells were cultured alone in chemically defined medium, the cells exhibited regression and showed the loss of smooth endoplasmic reticulum and swelling of the mitochondria. These changes were not prevented by the addition to the medium of either LH which stimulates Leydig cells or FSH which stimulates Sertoli cells.

In contrast, the co-culturing of Leydig and Sertoli cells resulted in Leydig cells that retain the smooth endoplasmic reticulum at the same level as exhibited in Leydig cells from intact animals. Furthermore, the addition of FSH to the co-culture appeared to stimulate Leydig cell development. (Tabone, et al., '84). Such observations have led numerous investigators to search in various unfractionated biological fluids from the testes for factors which affect Leydig cell function. These studies have led to the identification of both inhibitory and stimulatory activities.

Stimulatory activities include a group of biological activities that appear to be stable to heat, acids, or organic solvents and are capable of increasing both basal and LH-stimulated testosterone secretion. These factors have an average molecular weight of between about 5,000 and about 10,000. (Syed Int. J. Androls' '86) (Sharp & Cooper '84).

Other investigators have identified another group of Leydig cells stimulatory activities that are heat and enzyme sensitive and appear to be proteins with average molecular weights between about 10,000 and 60,000. These factors can also stimulate both basal and LH-stimulated testosterone secretion. (Sharpe INSERM '84); (Sharp & Bartlett '85); (Sharp Mol. Cell Endo. '88); (Benahmed Am. J. Phys. '85); (Benahmed J. Ster. Biochem '86); (Parvinen Mol. Cell Endo. '84); (Papadopoulus '87a); (Papadopoulus '87b); (Verhoeven & Cailleau '85); (Verhoeven & Cailleau '87); (Janecki Mol. Cell Endo. '85); (Jansz Biol. Reprod. '87); and (Liu & Dahl '88).

The present inventors have isolated a hitherto unknown protein which has important and unique functionalities and which has potentially significant therapeutic properties. This factor, known as Leydig Cell Stimulator, or "LCS", acts in ways which are not characteristic of other identified stimulatory factors. Furthermore, LCS acts to enhance and in some instances synergistically enhance the production of androgens such as testosterone when co-administered with LH/CG. This discovery not only provides a better overall understanding of the interplay between Sertoli cells and Leydig cells, but may also be useful in the treatment of infertility, low sperm count, premature or late onset of puberty as well as other conditions.

OBJECTS AND SUMMARY OF THE INVENTION

One object of the present invention is to provide a method of isolating LCS of a substantially pure and isolated form.

Another of the objects of the present invention is the provision of a Leydig cell stimulator or "LCS" which is present in a substantially pure and isolated form.

In accordance with the present invention these and other objects have been realized by the discovery of a process of isolating LCS. LCS is a polypeptide having a Mr between about 17,000 and about 20,000 as determined by SDS-PAGE characterized by the ability to stimulate at least about a 200 percent increase in androgen secretion by Leydig cells as compared to the cells' basal androgen secretion level.

In accordance with one embodiment of the isolation method of the present invention, the method includes the steps of providing a primary Sertoli cell-enriched culture medium, fractioning said medium by sequential HPLC on a preparative anion-exchange column, collecting and pooling the fractions corresponding to peak 1, subjecting the pooled peak 1 fractions to separation through a preparative gel permeation column, collecting and pooling the fractions between peaks 2 and 3, submitting the pooled fractions between peaks 2 and 3 to further separation by C4 reversed-phase HPLC, collecting and pooling the fractions corresponding to peak 1 subjecting the pooled peak 1 fractions to diphenyl--reversed-phase HPLC, collecting and pooling the fractions of peak 3, subjecting the pooled fractions of peak 3 to C18 reversed-phase HPLC and collecting the fractions eluting corresponding to peak 4.

In accordance with another aspect of the present invention there is provided an isolated and substantially pure Leydig cell stimulator which is a peptide having an Mr between about 17,000 and about 20,000 as determined by SDS-PAGE characterized by the ability to stimulate at least a 200 percent increase in androgen secretion by Leydig cells as compared to the cells' basal androgen secretion level.

As used herein, by the term "significant increase in androgen secretion," it is understood that when LCS is administered to Leydig cells, the level of increased androgen secretion resulting therefrom is significantly higher than that which could be realized by the administration of a functionally equivalent dose of any other known stimulatory factor. In fact, the administration of LCS to Leydig cells can produce at least 200 percent increase in the level of androgen secretion as compared to basal levels and often can produce an increase as much as 300 percent greater or more. In contrast, those known stimulatory factors which can independently evoke increased androgen secretion, are incapable of producing levels of increase of more than about 100 percent over basal levels. "Basal levels" or "basal androgen secretion levels" refers to the level of androgen produced by Leydig cells after they are removed from an animal and placed in culture as in EXAMPLE III.

LCS identified and isolated in accordance with the present invention has properties which make it unique. Clearly, LCS is not LH. The average molecular weight of LCS is between approximately 17,000 and about 20,000 as determined by SDS-PAGE, while LH, and in fact, CG, has an approximate molecular weight of about 28,500. Other data supports the differences between these compounds as well. For example, LH and CG are composed of two subunits, while LCS is composed of a single polypeptide. In addition, the antibodies against LH and CG do not react with LCS. Furthermore, LH/CG and LCS appear to operate on the basis of entirely different biochemical mechanisms. Specifically, LH/CG stimulates the production of cyclic AMP (cAMP) in Leydig cells upon binding to the Leydig cell receptor. When LCS binds to Leydig cells, no similar increase in cAMP is apparent.

Like LH/CG, however, LCS, acting on its own, can stimulate a significant increase in the secretion of androgen by Leydig cells when compared to basal levels. In fact, LCS-treated Leydig cells secrete androgen at levels which may, in some cases, approximate the levels of androgen secretion resulting from the exposure of Leydig cells to a maximal stimulatory dose of LH/CG. When LCS is used to treat certain Leydig cells, such as immature rat cells, the level of androgen secretion can exceed that resulting from the exposure of the same cells to a maximal stimulatory dose of LH/CG.

As illustrated in Table 1, no other known and characterized stimulatory factor which affects Leydig cells appears to be capable of independently producing such levels of androgen secretion.

TABLE 1

| Name | Stimulates Basal Testosterone | % Increase Over Basal When Admin. Alone | Reference |
| --- | --- | --- | --- |
| Insulin-like growth factor-1 | yes | 50-80% | 1, 2 |
| Fibroblast growth factor | yes | 100% | 3 |
| Inhibin | no | 0 | 4, 5 |

1. Lin, T. et al. Endocrinology 119:1641, 1986
2. Rigandiere, N. International Journal of Andrology 1:165, 1988
3. Sordoillet, Molecular and Cellular Endocrinology 58:283, 1988
4. Hsueh, A. Proceedings of the National Academy of Science 84:5082, 1987
5. Lin, T. Endocrinology 125:2134, 1989

But perhaps the most startling and unexpected property of LCS is its ability, when administered in combination with LH/CG, to provide levels of androgen secretion which are greater than those which could be realized by the administration of a maximal dose of LH/CG, alone. Previously, it was a widely held belief that the amount of androgen secreted by Leydig cells when subjected to a maximal stimulatory dose of LH/CG was the highest level of androgen secretion which could be realized from Leydig cells. The present inventors have unexpectedly found that by co-administering LH/CG with LCS, levels of androgen secretion may be significantly increased. This discovery is particularly startling when it is considered that the combination of other stimulatory factors with LH can provide no higher level of androgen secretion than that realized by the treatment of Leydig cells with a maximal stimulatory dose of LH/CG alone.

It is also an object of the present invention to provide a pharmaceutically active composition useful for stimulating and enhancing the production of androgen in animals in need of such treatment.

In accordance with the present invention there are provided a number of pharmaceutical preparations which can be used for these purposes. These pharmaceutical compositions are pharmaceutically active compositions useful for stimulating and enhancing the production of androgen in animals in need of such treatment which include: a pharmaceutically acceptable carrier and Leydig Cell Stimulator which is a polypeptide having an Mr of between about 17,000 and about 20,000 as determined by SDS-PAGE characterized by the ability to stimulate at least about a 200 percent increase in androgen secretion by Leydig cells as compared to said cells' basal androgen secretion level. The Leydig cell stimulator is provided in an amount effective to stimulate and enhance androgen production. Pharmaceutical compositions in accordance with this aspect of the present invention are useful for treating those androgen-related conditions described herein. However, these compositions are particularly useful for the treatment of patients who have low levels of, or an absence of, LH/CG receptors. This may result when patients have high levels of LH due to primary testicular failure. High levels of LH may "down regulate" and reduce the number of operable LH/CG receptors. Similarly, patients with Leydig cell "aplasia" do not develop normal Leydig cells because they either do not have LH/CG receptors or their receptors are disfunctional.

These pharmaceutical compositions may also include a pharmaceutically active composition useful for stimulating and enhancing the production of androgen in animals in need of such treatment which includes: a pharmaceutically acceptable carrier; a first amount of a Leydig cell stimulator polypeptide having a Mr of between about 17,000 and about 20,000 as determined by SDS-PAGE, characterized by ability to stimulate at least about a 200 percent increase in androgen secretion by Leydig cells as compared to said cells, basal androgen secretion level; and LH/CG provided in a second amount. The first and second amounts of LCS and LH/CG respectively are sufficient and effective to stimulate androgen production by Leydig cells greater than or equal to that resulting from the exposure of Leydig cells to either said first amount of LCS or said second amount of LH/CG.

A pharmaceutical composition including both LH/CG and LCS could provide a higher level of androgen production than could otherwise be expected. Such a pharmaceutical composition could have dramatic effects with regard to an animal suffering from infertility and/or from insufficient androgen production. For example, if an organism exhibits a low sperm count as a result of low testosterone levels due to some percentage of non-viable Leydig cells, the use of the composition of the present invention, including both LH/CG and LCS, could be administered to increase the production of testosterone by the remaining, viable Leydig cells. Therefore, methods of using LCS, either alone or in combination with LH/CG, as a treatment for low androgen secretion related conditions are specifically contemplated by the inventors.

Furthermore, because the present inventors have discovered that the secretion of LCS by the Sertoli cells is directly linked to the binding of FSH thereto, it may be possible to increase the production of androgen by increasing the FSH provided to Sertoli cells. This would start a chain of reactions which should include the stimulation and release of LCS and the subsequent stimulation of androgen production. The use of LH/CG and FSH to increase the production of androgen is also contemplated hereby.

Another object of the present invention is to provide a convenient source of substantially pure LCS.

In accordance with this aspect of the present invention there is provided a host cell including non-native DNA capable of expressing a polypeptide having a Mr of between about 17,000 and about 20,000 as determined by SDS-PAGE, characterized by the ability to stimulate at least about a 200 percent increase in androgen secretion by Leydig cells as compared to said cells' basal androgen secretion level.

BRIEF DESCRIPTION OF THE DRAWINGS

Preferred embodiments of the present invention will be described in greater detail with reference to the accompanying drawings wherein.

DETAILED DESCRIPTION OF THE PREFERRED EMBODIMENTS

Figure 1:
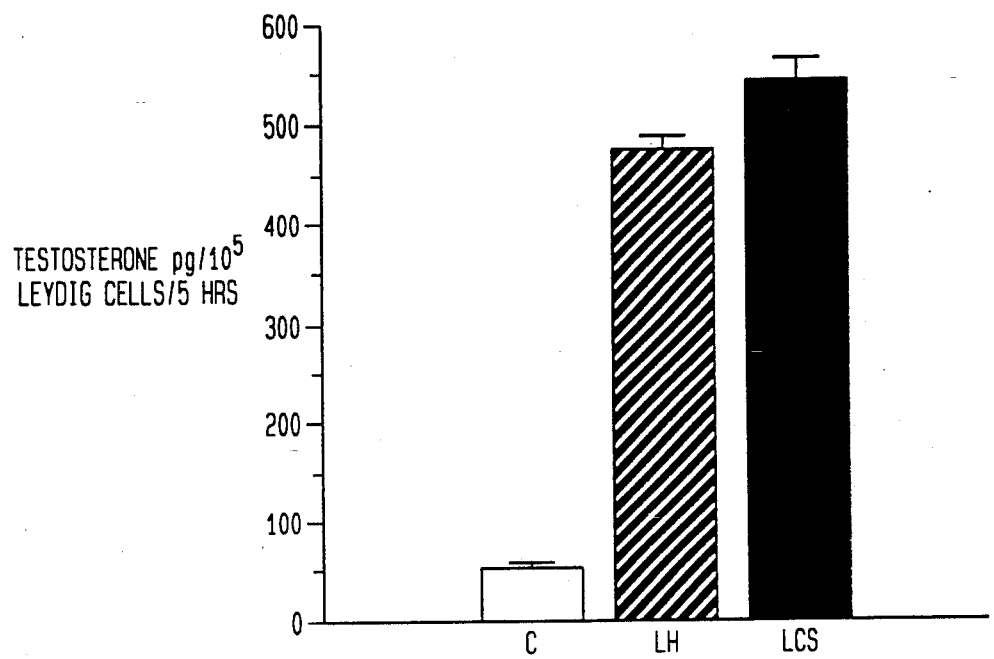
FIG. 1 graphically illustrates the level of testosterone produced by immature rat Leydig cells upon application of nothing (C), LH, or LCS.

The inventors have discovered and isolated a protein whose existence and activity are both surprising and unexpected. After the purified LCS was resolved by SDS-PAGE under both reducing and non-reducing conditions on a 12.5% T SDS-polyacrylamide gel, it was determined that LCS has an apparent Mr of between about 17,000 and about 20,000, and more preferably about 17,000. It was also discovered that LCS is a single polypeptide chain.

LCS can be characterized in a number of ways such as by its amino acid sequence. For example, LCS has an amine-terminal region having the structure of (SEQ. ID NO. 1). However, because of the unique activity associated with LCS, perhaps the best way to characterize this peptide is by its characteristic activity.

One way to use the activity of the LCS for characterization purposes is by comparing LCS to the compounds which are most like it in their ability to stimulate the secretion of androgen; namely LH/CG. Like LH/CG, LCS is capable of stimulating significant increases in androgen secretion above the basal level of secretion of Leydig cells. In some circumstances, the amount of androgen secreted by Leydig cells due to the exposure of those cells to LCS, begins to approximate the levels obtainable by administration of a functionally equivalent dosage of LH/CG. In any event, the amount of hormone secreted by the use of LCS is substantially closer to the amounts realized by the use of LH/CG than those realized by the use of any other known stimulatory factor.

Compare for example, the results obtained by the application of LCS, hCG, and a mixture of LCS and hCG in comparison to other stimulatory factors as described in TABLE 2.

TABLE 2

Effects of the Leydig Cell Stimulator (LCS) isolated according to the procedures of EXAMPLE II from Sertoli cell-enriched culture media on mature Leydig cell steroidogenesis. Mature Leydig cells were prepared according to the procedures described in EXAMPLE III and the bioassay for LCS was accomplished according to the procedures described in EXAMPLE IV. HCG was used as a positive control TABLE 2-continued

| Sample | Testosterone (ng/5 × 10⁴ cells/24 hr)* |
|---|---|
| Leydig cells alone | 30 ± 8 |
| Purified LCS (5 ng/culture well) | 120 ± 10 |
| hCG (1 ng/culture well) | 150 ± 20 |
| hCG (1 ng/culture well) plus purified LCS (5 ng/culture well) | 180 ± 20 |

*All data are mean ± SD of a given experiment consisting of three replicates. These experiments have been repeated at least three times using different batches of samples and similar results were obtained in each instance.

In contrast, and with reference to the known stimulatory activities recited in Table 1, the administration of a maximal stimulatory dose of fibroblast growth factor to Leydig cells should produce no more than a 100 percent increase over basal levels. Using the numbers recited in Table 2, the result of such an application would be testosterone levels of approximately 60 as compared to 120 obtained by the use of purified LCS and 150 for hCG. Table 2 also indicates that, because of the calculated error, purified LCS could provide the same level of stimulatory activity as hCG or LH.

In fact, with certain types of Leydig cells such as immature rat Leydig cells, the administration of LCS may result in the realization of a level of androgen production that is greater than that obtainable by the use of LH/CG. With reference to FIG. 1, the application of a maximal stimulatory dose of LH to immature rat Leydig cells produced a lower level of testosterone secretion than the exposure of such Leydig cells to a maximal stimulatory dose of LCS.

Figure 2:
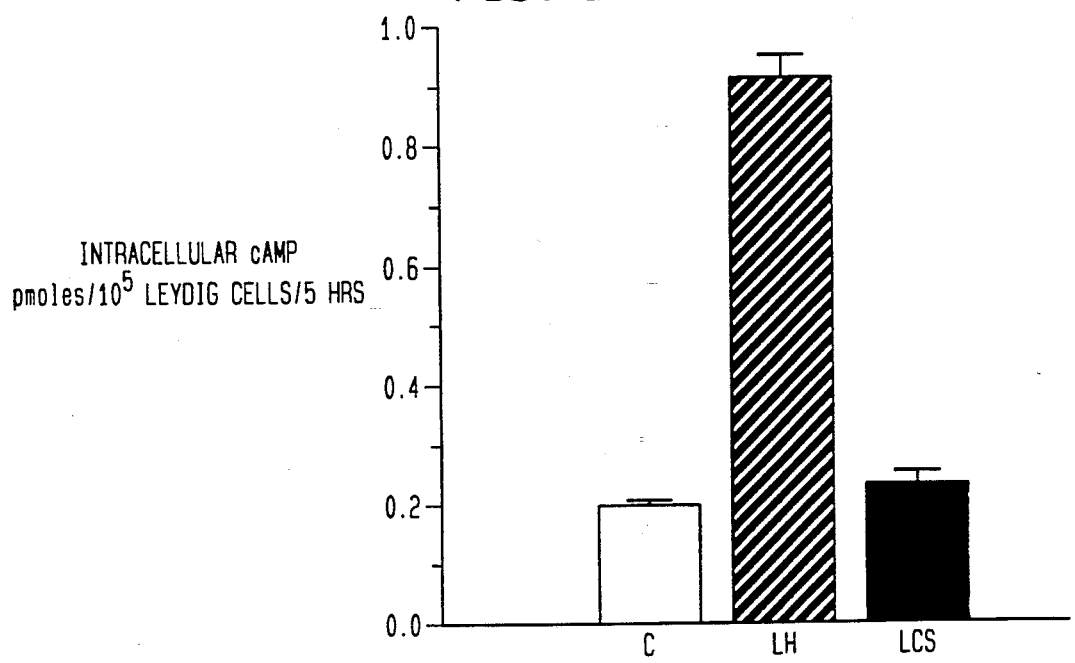
FIG. 2 graphically illustrates the level of intracellular cAMP accumulated resulting from the exposure of immature rat Leydig cells to nothing (C), LH, or LCS.

Similarly, LCS can be characterized by its mode of androgen stimulation. As shown in FIG. 2, the application of a maximal stimulatory dose of LH to immature rat Leydig cells produced a significant increase in cAMP. In contrast, the application of a maximal stimulatory dose of LCS to immature rat Leydig cells produced no significant increase in intracellular cAMP accumulation.

LCS can also be characterized by comparing it to other known stimulating factors. When other stimulating factors are administered to Leydig cells, alone, the results can be generalized into one of two categories. The first category as shown in Table 1, includes those factors which induce no additional stimulation. These stimulatory compounds are only effective if co-administered with LH. This is clearly different from LCS as LCS is capable of independently producing significant increases in androgen secretion by Leydig cells. The second group of compounds, as also shown in Table 1, can produce a measurable increase in androgen secretion. However, the amount of androgen secretion in relation to basal levels, is dramatically less than that which can be realized by the use of LCS. The greatest percentage increase known to result from the use of some other stimulatory factor is 100 percent greater than basal levels. See Table 1.

In contrast, LCS has the ability to increase androgen secretion of Leydig cells by at least about 200 percent as compared to these cells basal levels. Indeed, increases of 300 percent or more may also be realized. See Table 2.

Figures 3, 4:
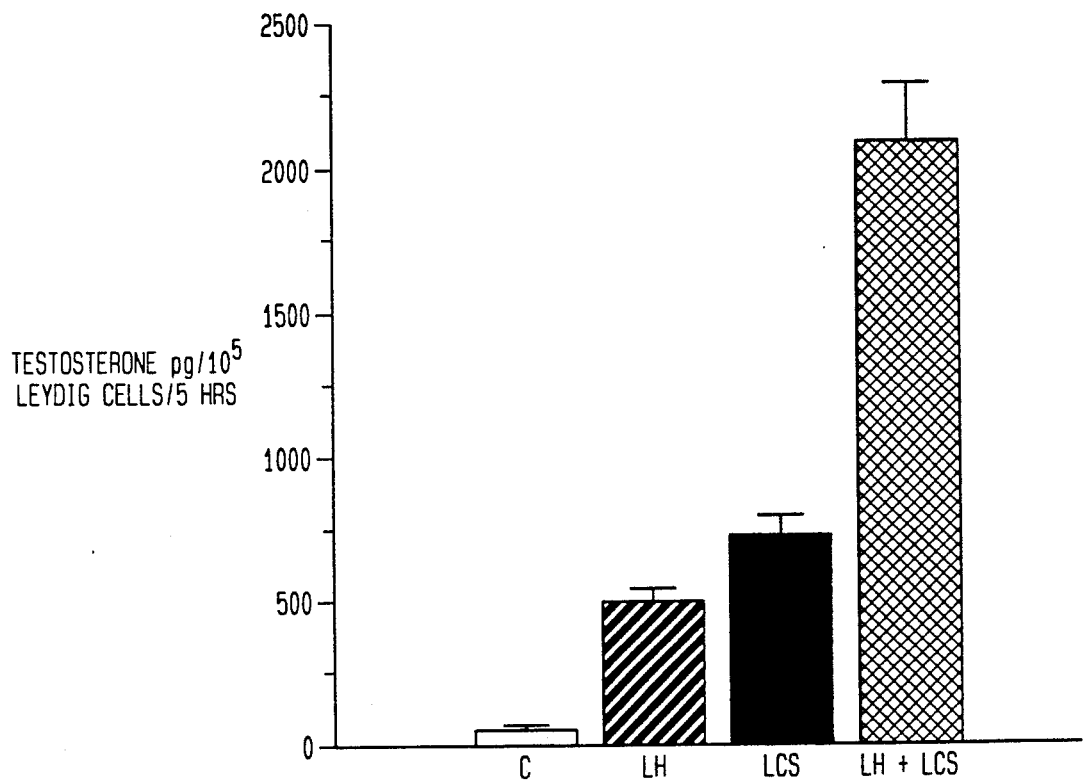
FIG. 3 graphically illustrates the level of testosterone produced by the individual application of nothing (C), LH, LCS and by the combined application of LH and LCS to immature rat Leydig cells.
FIG. 4 illustrates the amino acid sequence of the amine-terminal or N-terminal region of LCS.

Most importantly, however, when any of the known stimulatory factors are added to a maximal stimulatory dose of LH/CG, the resulting level of androgen secretion is no greater than that which could be realized by the administration of that dosage of LH/CG, alone. In contrast, the level of androgen secretion realized by the administration of LCS and a maximal stimulatory dosage of LH/CG is higher than that which could realized by the administration of a maximal stimulatory dose of LH/CG alone. As illustrated in Table 2, testosterone secretion from mature Leydig cells when exposed to a maximal stimulatory dose of LCS, alone, was about 120. The level of testosterone secreted by mature Leydig cells when exposed to hCG alone was about 150. It was found, quite unexpectedly, that when the maximal stimulatory dose of LCS and hCG were administered to mature Leydig cells, simultaneously, the resulting level of testosterone secretion was 180. More dramatic results were obtained when the same procedure was carried out on immature rat Leydig cells. As shown in FIG. 3, LCS provided an increased level of testosterone secretion when applied to immature Leydig cells alone and when compared to the level of testosterone secreted by LH. In fact, the administration of LH to these Leydig cells resulted in approximately an eight to nine fold increase of testosterone secretion. The use of a maximal stimulatory dose of LCS produced approximately an eight-to-twelve-fold increase in testosterone secretion. When the maximal stimulatory doses of LH and LCS were combined and administered to these Leydig cells, a synergistic level of testosterone secretion resulted. In fact an approximately 35 fold increase in testosterone secretion was realized.

LCS is a naturally occurring protein in male animals. However, obtaining LCS in an isolated, purified and useable form is complicated because of the complexity of intra-testicular fluid. One method of obtaining LCS in a purified and usable form is by the use of complex separation procedures. One preferred procedure generally involves the preparation of a Sertoli cell-enriched culture. This is accomplished by removing aggregates of Sertoli cells recovered from enzymatic treatment of the seminiferous tubules of an animal. These cells are recovered, isolated, plated in plastic culture dishes and mixed with a suitable medium. While in the media, the Sertoli cells naturally produce LCS which can be collected and separated from the Sertoli cell-enriched culture medium by a complex series of separation steps such as those described in EXAMPLE II. Once LCS has been purified by the separation procedure noted above, the N-terminal amino acid sequence analysis can be performed.

One of the major goals of performing N-terminal sequence analysis is to define the identity of the purified protein following its comparison with existing protein and gene database. N-terminal sequence analysis will be performed on peptide fragments following tryptic/-protease V8/CNBr fragmentations (Cheng, C. Y., Musto, N. A., Gunsalus, G. L., Frick, J., and Bardin, C. W. (1985) *J. Biol. Chem.* 260:5631–5640; Hammond, G. L., Underhill, D. A., Smith, C. L. Goping, I. S., Harley, M. J., Musto, N. A., Cheng, C. Y., and Bardin, C. W. (1987) *FEBS Letts.* 215:100–104; and Gross, E. (1967) *Meth. Enzymol.* 11:238–255) to yield enough seqence information for preparation of antibodies against peptide fragments and to prepare oligonucleotides for gene cloning experiments. The peptide fragments will either be separated by SDS-PAGE, transferred onto PVDF membrane and sequenced; or by C18 reversed-phase HPLC. The former procedure will be useful to generate sufficient sequence data for subsequent studies if the protein of interest cannot be purified to apparent homogeneity, whereas the latter procedure will be the technique of choice since about 30-50 PTH(phenylthiohydantoin)-amino acids can be determined in a single sequence experiment. To determine cysteine (cys), the reactive thiol group will be neutralized by appropriate chemical procedures through S-alkylation with 4-vinylpyridine as previously described (Hawke, D. and Yuan, P. (1987) *Applied Biosystems User Bull.* 28:1-8). The N-terminal or amine-terminal region of LCS is identified as (SEQ. ID NO. 1) and is illustrated in FIG. 4. Xaa is one of the naturally occurring amino acids.

Once part of the amino acid sequence is known, specific polyclonal antibodies can be prepared. Polyclonal antibodies will be prepared using established procedures (Vaitukaitis, J. L., Robbins, J. B., Nieschlag, E., and Ross, G. T. (1971) *J. Clin. Endocrinol. Metab.* 33:988-991) as previously described (Cheng, C. Y. and Bardin, C. W. (1987) *J. Biol. Chem.* 262:12768-12779; Cheng, C. Y., Mathur, P. P., and Grima, J. (1988) *Biochemistry* 27:4079-4088; and Cheng, C. Y., Bardin, C. W., Musto, N. A., Gunsalus, G. L., Cheng, S. L. and Ganguly, M. (1983)*J. Clin Endocrinol. Metab.* 56:68-75). However, in cases where obtaining a sufficient quantity of proteins becomes impractical, the P.I. proposes to prepare polyclonal antibodies against synthetic peptide fragments which will be constructed using information obtained from protein sequence analysis of internal fragments. Chemical synthesis of 10 to 30 amino acid residues will be performed by the solid-phase method (Merrifield, R. B. (1963) *J. Am. Chem. Soc.* 85:2149-2154) at the Rockefeller University Protein Chemistry Core Facility. The synthetic peptide will then be cross-linked to poly-L-lysine by established procedures (Posnett, D. N., McGrath, H., and Tam, J. P. (1988) J. Biol. Chem. 263:1719-1725). Briefly, 0.5 mg of the synthetic peptide will be reacted with 0.5 mg of carbodiimide and the synthetic peptide will be coupled to poly-L-lysine hydrobromide (Mr 30,000-70,000). This will be used as the source of immunogen for preparation of polyclonal antibodies. Monospecificity of the antisera will be determined by crossed immunoelectrophoresis or immunoblots as detailed elsewhere (Cheng, C. Y. and Bardin, C. W. (1986) *Biochemistry* 25:5276-5288; Cheng, C. Y. and Bardin, C. W. (1987) *J. Biol. Chem.* 262:12768-12779; Cheng, C. Y., Mathur, P. P., and Grima, J. (1988) *Biochemistry* 27:4079-4088).

Amongst the major objectives of producing polyclonal antibodies is to permit the identification of complimentary DNA (cDNA) coding for LCS. This cDNA will be transfected into an appropriate host cell. Rat testicular cDNA λ gt11 expression libraries will be screened with monospecific polyclonal antibodies (Young, R. A. and Davis, R. W. (1983) *Proc. Natl. Acad. Sci. USA* 80:1194-1198) and the clones containing cDNA coding for these factors will be further characterized by epitope selection (Weinberger, C., Hollenberg, S. M., Ong, E. S., Harmon, J. M., Bower, S. T., Cidlowski, J., Thompson, E. B., Rosenfeld, M. G., and Evans, R. M. (1895) *Science* 228:740-742) as previously described (Cheng, C. Y., Chen, C.-L. C., Feng, Z. M., Marshall, A., and Bardin, C. W. (1988) *Biochem. Biophys. Res. Commun.* 155:398-404). If a full-length cDNA cannot be obtained using this approach, a synthetic oligonucleotide probe will be synthesized based on the partial N-terminal and internal amino acid sequences, or nucleotide sequences and will be used as an alternative screening approach (Hammond, G. L., Underhill, D. A., Smith, C. L., Goping, I. S., Harley, M. J., Musto, N. A., Cheng, C. Y., and Bardin, C. W. (1987) *FEBS Letts.* 215:100-104). A library will be screened with [$^{32}$P]-labeled synthetic oligonucleotide probes (Wallace, R. B., Johnson, M. J., Hirose, T., Miyake, T., Kawashima, E. H., and Itakura, K. (1981) *Nucleic Acids Res.* 9:879-894). In the case of very low abundance sequences, synthetic oligonucleotides will be used as primers for the polymerase chain reaction (PCR). The PCR procedure will be used to amplify specific cDNAs from mRNA preparations by synthesis from an internal oligonucleotide primer and oligo dT (Berchtold, M. W. (1989) *Nucleic Acids Res.* 17:453). The cDNA thus obtained will be used to determine the complete sequence of LCS as described herein, and for production of LCS in host cells.

Restriction endonuclease will be used to cleave the cDNA insert from the γ DNA, this insert will be subcloned into pGEM/-3Z vector and sequenced as previously described (Cheng, C. Y., Chen, C.-L. C., Feng, Z. M., Marshall, A., and Bardin, C. W. (1988) *Biochem. Biophys. Res. Commun.* 155:398-404; and Tabor, S. and Richardson, C. C. (1987) *Proc. Natl. Acad. Sci. USA* 84:4767-4771). This will provide the entire amino acid sequence of LCS.

Another method for obtaining a cDNA or genomic DNA sequence encoding for LCS with appropriate regulatory signals such as a gene promoter sequence and a gene terminator sequence appended thereto is also provided hereby. After expression of the gene sequence encoding for this peptide in the host cell, LCS can be collected either from the surrounding spent media, (if the protein is excreted by the host cell) or by destroying the host cell and separating LCS therefrom.

The host cell for this process can be either procaryotic, for example, a bacteria cell, or eucaryotic, for example a plant or animal cell. For the purposes of large scale production, microbial hosts such a bacteria or yeast may be used. Alternatively, other gene expression systems can be used for production of these peptides such as those involving cultured mammalion cells.

Genes encoding LCS, for example, can be prepared entirely by chemical synthetic means or can consist in part of a portion or all of a sequence derived from natural sequences encoding a peptide. Chemical synthesis of oligonucleotides composed entirely of deoxyribonucleotides can be achieved through application of solution chemistries or can be preferably carried out on solid supports. Several synthesis chemistries for oligonucleotides have been devised and include phosphotriester, phosphite-triester and phosphoramidite chemistries. See M. H. Caruthers, "New methods for chemically synthesizing deoxyoligonucleotides" in *Methods of DNA and RNA Sequencing* (S. M. Weissman, Ed.; Praeger Publishers, New York), (1983), 1-22, and K. Itakura et al., "Synthesis and use of synthetic oligonucleotides:, *Ann. Rev. Biochem.* 53, (1984), 323 356. Phosphoramidite synthesis chemistries such as those involving N,N-dimethylaminophosphoramidites or beta-cyanoethyl-diisopropylaminophosphoramidites or deoxyribonucleoside-morpholino-methoxyphosphines are preferred because of their efficient coupling of nucleotides to a growing oligonucleotide chain and for the stability of the chemical reagents employed. The most preferred phosphoramidite chemistries are those employing beta-cyanoethyl-diisopropylamino-phosphoramidites because of their extended stability relative to comparable intermediates and their avoidance of toxic reagents such as thiophenol. See, S. L. Beaucage and M. H. Caruthers, "Deoxynucleoside phosphoramidites—a new class of key intermediates for deoxypolynucleotide synthesis", *Tetrahedron Lett.* 22, (1981), 1859–1862; L. J. McBride and M. H. Caruthers, "An investigation of several deoxynucleotide phosphoramidites useful for synthesizing deoxyoligonucleotides", *Tetrahedron Lett.* 24, (1983), 245–248; T. Dorper and E. L. Winnacker, "Improvements in the phosphoramidite procedure for the synthesis of oligodeoxyribonucleotides", *Nuc. Acids Res.* 11, (1983) 2575–2584; and S. P. Adams et al., "Hindered dialkylamino nucleoside phosphite reagents in the synthesis of two DNA 51-mers", *J. Amer. Chem. Soc.* 105, (1983), 661–663. Phosphoramidite chemistries on solid supports in brief consist of attaching a modified nucleotide to a solid material such as glass, silica gel, polyacrylamide, cellulose, polystyrene, nitrocellulose or some other generally chemically inert material. The nucleotide phosphate group and any exocyclic nitrogen atoms in the nucleotide base are protected on such supports with chemical groups so as to prevent unwanted side reactions during linear elongation of the oligonucleotide chain. Such attachments can be through a variety of linker or spacer moieties, but preferred linkers are generally long chain alkyl amines. See M. D. Matteucci and M. H. Caruthers, U.S. Pat. No. 4,458,066. The attached nucleotide is protected at the 5' sugar position with an acid labile dimethoxytrityl chemical group which is removed with an acid such as benzenesulfonic acid, trichloroacetic acid or dichloracetic acid to free a 5'-OH group for coupling, thereby beginning linkage of additional nucleotides. Preferred acids for this deblocking or activation step are dichloroacetic acid or trichloracetic acid. A phosphoramidite monomer nucleoside protected similarly to the nucleotide attached to the solid support is then added in the presence of a weak acid to promote nucleophilic attack of the 5'-OH group on the phosphoramidite reagent. Preferred weak acids for the coupling step include tetrazole, amine hydrochlorides, and 3-nitrotriazole, with the most preferred weak acid being tetrazole. Failed coupling sites on the solid support are then blocked or capped by acetylation of free hydroxyl groups with acetic anhydride. A preferred coreactant in the capping step is 1-methylimidazole. The natural internucleotide phosphate diester linkage is subsequently generated at each cycle of nucleotide addition by treatment of the growing nucleotide chains on the solid support with a mild oxidation mixture. This oxidation step converts phosphorus (III) to the more stable phosphorus (V) oxidation state and prevents nucleotide chain scission at any subsequent deblocking or activation treatment steps by acid species such as dichloroacetic acid or trichloroacetic acid. Iodine is used as the oxidizing species with water as the oxygen donor. Preferred coreagents include tetrahydrofuran and lutidine. Following a wash of the solid support with anhydrous acetonitrile, the deblock/coupling/oxidation/capping cycle can be repeated as many times as necessary to prepare the oligonucleotide or oligonucleotides of choice, each time using the appropriate protected betacyanoethylphosphoramidite nucleoside to insert the nucleotide of choice carrying a purine or pyrimidine base. The purine bases preferably will be either adenine or guanine on the inserted nucleotide and the pyrimidine bases preferably will be cytosine or thymine. The simplicity of chemical synthesis of oligonucleotides has led to the development of practical guides for laboratory work and common use of commercial automated DNA synthesizers. See, M. H. Caruthers, "Gene synthesis machines: DNA chemistry and its uses", *Science* 230, (1985), 281–285; and J. W. Efcavitch, "Automated system for the optimized chemical synthesis of oligodeoxyribonucleotides" in *Macromolecular Sequencing and Synthesis, Selected Methods and Applications* (Alan R. Liss, Inc., New York), (1988), 221–234. Commercial instruments are available from several sources such as DuPont Company (Wilmington, Del.), Milligen/BioSearch, Inc. (San Rafael, Calif.) and Applied Biosystems (Foster City, Calif.).

The last coupling cycle of oligonucleotides can be completed leaving the 5' terminal dimethoxytrityl group on or off. The dimethoxytrityl group is preferably left on for convenience in subsequent purification of full-length oligonucleotides. The completed and protected oligonucleotides must be deprotected and cleaved from the solid support prior to purification. The solid support bearing the completed oligonucleotides is treated with fresh concentrated ammonium hydroxide at room temperature for at least one hour to cleave the oligonucleotides from the support resin. The solid support is then washed with more concentrated ammonium hydroxide and the combined concentrated ammonium hydroxide is incubated at 55°–60° C. for at least eight hours in a sealed vial in order to remove the protecting chemical functionalities from the protected bases. The sample is then cooled and evaporated to dryness under vacuum. The sample may also be re-evaporated from fresh concentrated ammonium hydroxide or ethanol of at least 95% purity by volume. The final sample can then be stored in a lyophilized (dry) state or can be re-suspended in sterile distilled water before storage at −20° C. See the PCR-Mate Model 391 user's manual, supra, and M. H. Caruthers et al., "Chemical Synthesis of Deoxyoligonucleotides by the Phosphoramidite Method," *Methods in Enzymology* 154, (1987), 287–313.

Any cleaved and deprotected oligonucleotides prepared by methodology drawn from the preferred choices above can be purified by one or more of several methods known in the art. These purification techniques include but are not limited to polyacrylamide gel electrophoresis, agarose gel electrophoresis, size exclusion chromatography, affinity chromatography, high performance liquid chromatography and hydrophobic interaction chromatography. The preferred method is selected from the group of purification techniques which consists of polyacrylamide gel electrophoresis, high performance liquid chromatography and hydrophobic interaction chromatography. One such preferred method is preparative polyacrylamide gel electrophoretic purification of oligonucleotides, lacking a dimethoxytrityl moiety on the 5' terminus, on a vertical 12% polyacrylamide slab gel, 20×20×0.15 cm, in 7M urea, 90 mM Tris-HCl, pH 8.3, 90 mM borate, 1–2 mM disodium ethylenediaminetetraacetic acid (EDTA). A portion of each oligonucleotide to be purified (0.3–3.0 $A_{260}$ units) is evaporated to dryness under vacuum, re-suspended in formamide:1 mM disodium EDTA (greater than 9:1) containing at least 0.01% bromophenol blue and at least 0.01% xylene cyanol, heated 2–3 minutes in a boiling water bath, quickly placed in an ice slurry and then loaded in an individual well (at least 6 mm in width). The sample(s) is electrophoresed at 40–45 W towards the anode until the bromophenol blue has migrated at least two-thirds the length of the polyacrylamide gel. The full-length oligonucleotides are then visualized by placing the polyacrylamide gel on a piece of flexible, clear plastic wrap such as Saran Wrap, placing it on top of a thin layer chromatography plate (e.g., Silica Gel F-254; Fisher Scientific Company, Pittsburgh, Pa.) containing a fluorescent indicator compound and examining the polyacrylamide gel under short wavelength ultraviolet light illumination. The full-length band material is then excised in polyacrylamide and can be purified out of the gel by various methods such as electroelution or simple diffusion in buffer. The preferred method of extraction is diffusion into 0.5 mL of 0.3M sodium acetate, pH 7.5, overnight with shaking and successive extractions of the aqueous phase with phenol:chloroform (1:1, v:v) and ethanol precipitation. The precipitated oligonucleotide can then be re-suspended in an appropriate volume (usually in the range of 10-1000 microliters) of a suitable buffer such as 10 mM Tris-HCl, pH 7.5, 1 mM disodium EDTA or in sterile distilled water and stored at −20° C. See unit 2.12, "Purification of oligonucleotides using denaturing polyacrylamide gel electrophoresis," in *Current Protocols in Molecular Biology*, F. M. Ausubel et al., Eds., (1989).

An alternative more preferred method of purification and one well suited for purification of oligonucleotides still having a dimethoxytrityl moiety on the 5' terminus is high performance liquid chromatography (HPLC) on a reverse phase HPLC column. Such a reverse phase HPLC column can be packed with any of a variety of silica or polymer based resins which are commercially available from a number of vendors such as Millipore/Waters (Milford, Mass.), The Nest Group (Southboro, Mass.), Rainin Instrument Company, Inc. (Woburn, Mass.), J. T. Baker Inc. (Phillipsburg, N.J.), Alltech Associates Inc. (Deerfield, Ill.), or Pierce Chemical Company (Rockford, Ill.). Oligonucleotides are loaded, fractionated and eluted from such an HPLC column by, for example, an acetonitrile gradient in any of several suitable non-destructive buffers. Preferred acetonitrile gradients are in the range of 5% to 40% and more preferably in the range of 5% to 30% in 0.1M triethylammonium acetate, pH 7.0, buffer. Preferred reverse phase HPLC columns include those with linear alkyl chain moieties bound to them such as $C^4$, $C^8$, or $C^{18}$ alkyl chains. The appropriate fractions containing purified full-length oligonucleotide are then pooled, evaporated under vacuum and re-suspended in 3% (v/v) acetic acid in water at room temperature for 10-30 minutes. The detritylated oligonucleotides are then ethanol precipitated or purified by other suitable means such as size exclusion chromatography. Alternatively, full-length detritylated oligonucleotides can also be purified by HPLC using various types of columns and gradient materials. For guidance, see G. Zon and J. A. Thompson, "A review of high-performance liquid chromatography in nucleic acids research," *BioChromatography* 1, (1986), 22-32.

One or more synthetic oligonucleotides will be necessary to prepare a partially or completely synthetic gene for the purposes of the present invention. Any appropriate oligonucleotides and/or portions or all of a natural gene such as a natural LCS gene can be assembled into a gene encoding LCS by denaturing these DNAs by some means such as heating, mixing with a chaotropic agent such as urea or formamide or exposure to an alkaline solution. Phosphate moieties can be optionally attached enzymatically to any DNAs or oligonucleotides lacking them using an enzyme such as T4 polynucleotide kinase. See section 3.10 in *Current Protocols in Molecular Biology*, supra. Any oligonucleotides being used in the preparation of a gene within the scope of the present invention and in the presence or absence of any additional natural DNAs are then re-natured or annealed by appropriate means, such as slow cooling to room temperature or dialysis to remove any chaotropic agents. These annealed DNAs can be linked covalently by treatment with a suitable enzyme such as T4 DNA ligase. See section 3.14 in *Current Protocols in Molecular Biology*, supra.

If necessary and where suitable, the gene products encoding peptides prepared by this means can be prepared for appending to genetic regulatory DNA sequences by treatment with restriction endonucleases according to manufacturer's specifications or by methods known in the art. See, for example, T. Maniatis et al., *Molecular Cloning*, supra, pp. 104-106.

Genetic regulatory signals which are appended to genes encoding peptides so as to render them capable of expression as protein in a defined host cell may include gene promoter sequences, which are DNA sequences recognized by the biological machinery of the host cell and which induce transcription of the DNA sequence into messenger RNA (mRNA) by an RNA polymerase within the host cell. This mRNA must then be capable of being translated on ribosomes within the host cell into a protein product. The gene promoter sequences may be derived in part or in whole from promoter sequences found in cells unlike those of the host cell so long as they meet the above criteria for transcription and translation. One convenient way to accomplish this is to insert the complimentary DNA into an expression vector which has a promoter comprised of a TATA box and either a hormone or a metal response element. When this expression vector is transfected into an appropriate host cell, the host cell will produce LCS in large quantities in response to the hormone on the metal.

A second genetic regulatory element which may be appended to an LCS gene for the expression of LCS is a gene terminator or polyadenylation sequence. This DNA sequence contains genetic information that interrupts and halts further transcription, and, in the case of eucaryotic cells, provides information directing attachment of one or more adenosine nucleotides at the 3' end of the mRNA. A gene terminator sequence may represent in part or in whole a terminator sequence originating from the genome of the host cell or from the genome of some unlike cell that is known to be effective at appropriately terminating transcription within the host cell. An example of such a sequence would be the *Salmonella typhimurium his* operon rho-independent transcription terminator sequence (see, for example, M. E. Winkler, *Escherichia coli and Salmonella typhimurium: Cellular and Molecular Biology* [F. C. Neidhardt, Ed.-in-chief; American Society for Microbiology, 1987], chapter 25) or the octopine synthase terminator sequence from an *Agrobacterium tumefaciens Ti* plasmid (see, for example, H. DeGreve et al., "Nucleotide sequence and transcript map of the *Agrobacterium tumefaciens Ti* plasmid-encoded octopine synthase gene,", *J. Mol. Appl. Genet.* 1, (1982), 499-511).

A peptide expressing gene or genes with attached genetic regulatory signals is preferably introduced into a host cell of either procaryotic or eucaryotic origin for the intent of expressing LCS. The means of introduction is well-described in the art and depends upon the type of host cell in which gene expression is being sought. For example, transformation of bacterial cells with externally supplied DNA such as cells of *Escherichia coli* can be accomplished by a calcium chloride procedure. Typically, the peptide gene or genes with attached genetic regulatory signals are covalently bound into a suitable transformation vector prior to the transformation procedure. Such vectors have been reviewed in Vectors: a *Survey of Molecular Cloning Vectors and Their Uses* by R. L. Rodriguez and D. T. Denhardt (Butterworths, Boston; 1988). See, also T. Maniatis et al., *Molecular Cloning*, supra, pp. 247-255.

Once expressed with any such gene expression system in a suitable host cell, the peptide may be extracted and/or purified by conventional means. Methods of extracting peptide from host cells include heat and/or enzymatic lysis of the host cell, solubilization in a lipidic solvent or aqueous-organic micellar solution, and pressure rupturing of cell membranes and/or cell walls by forcing the host cells through a French press. The preferred method for cell lysis for the case of bacteria as host cells depends upon the scale of production being sought. For large scale production, heat or pressure rupturing of the bacterial cells is preferred. See, for example, H. Hellebust, "Different approaches to stabilize a recombinant fusion protein," *Bio/Technology* 7, (1989), 165-168. The extracted LCS may be used in its immediate form without further purification or may be partially or completely purified by application of one or more fractionations of cellular contents by a method such as size exclusion chromatography, ion exchange chromatography, electrophoresis, affinity chromatography and the like.

While LCS may be of great interest in that it provides a better understanding of the inter workings of the testes, the isolation of this peptide has much more profound pharmaceutical implications. The compositions of the present invention are useful for treating animals afflicted with androgen-based disfunctions, such as, for example, hypogonadotropic hypogonadism, anorchia, orchitis, Leydig cell aplasia, delayed puberty, and infertility.

When the pharmaceutical compositions of the present invention include only LCS for the purposes of increasing androgen secretion by Leydig cells, the amount of LCS provided depends upon a number of factors. First, the amount of LCS provided depends upon the size and weight of the patient in need of such treatment and upon the degree of enhanced androgen secretion that is desired. Furthermore, the amount of LCS administered in pharmaceutical compositions in accordance with the present invention depends in some degree upon the type of delivery vehicle used and how often those dosages are administered. A single maximum stimulatory dose of hCG (6,000 IU equals about 0.46 mg) will elevate serum testosterone above normal for four days in an adult male. A maximal stimulatory dose of LCS will provide similar results. Therefore, about 2.3 mg of LCS will be needed and must be administered two to three times a week for an adult male. Such treatment is often used to complete sexual maturation in individuals who do not complete their pubertal development because of Leydig cell aplasia, anorchia or orchitis. In clinical practice, less than maximal amounts of hCG are sometimes used at a dose of 1,000-2,000 IU every other day for the treatment of infertility and hypogonadotropic hypogonadism. Dosages of between about 0.4 and about 0.8 mg LCS administered every other day, could, therefore, provide similar effects. Thus, pharmaceutical compositions in accordance with the present invention may include from between about 0.1-5.0 mg of LCS and, more preferably, between about 0.4 and about 2.4 mg of LCS, and administration of this amount of LCS will be every day or every other day depending on the condition, the size of the patient, and other factors known to physicians. When the compositions in accordance with the present invention also include either LH or CG, the amount of LH/CG included will range from between about 0.1-0.46 mg.

While many methods of administering LCS to, for example, human males are contemplated, the preferred methods of administering LCS include intramuscular or subcutaneous injection. This is also the preferred method of administering LH, hCG and FSH. Of course, individual dosages of any of these compounds can be adjusted as needed in each individual based upon the serum testosterone levels during treatment. In accordance with the present invention, and to evoke the maximal testosterone secretion by Leydig cells, a dosage form including, for example, 0.46 mg of hCG and 2.3 mg of LCS (maximal stimulatory doses of hCG and LCS) would be administered. By so doing, it has been unexpectedly found that the level of androgen secretion will be greater than that obtainable by the use of a maximal stimulatory dose of LH alone which, until this discovery, was thought to be the highest level of androgen secretion possible.

Of course, pharmaceutically acceptable salts of LH/CG, FSH, or LCS may be administered.

The preferred dosage forms in accordance with the present invention are made by dissolving dry LCS in water. If, for example, 2.5 mg of LCS is to be administered, then preferably, 25 mg of LCS is dissolved in 10.0 cc of water. To this solution, a number of common excipients may be added. The most common excipients useful in accordance with the present invention for the preparation of parenteral dosage forms include D-mannitol or D-lactose 5% as a stabilizing agent, serum albumin, 0.1-1% concentration, to inhibit surface adsorption and act as a cryoprotectant during lyophilization; and/or sodium citrate or sodium acetate as a buffer if needed. If LCS, either alone or in combination with, for example, LH/CG is to be administered in a parenteral dilution instead of being lyophilized, 0.5% chlorobutanol or 0.01% thimerosol should be included in the formulation as a preservative. Thus, for example, the 2.5 mg/ml formulation described above may also include 5% D-mannitol, 0.5% serum albumin and sufficient buffer to maintain a pH of about 7.4.

The foregoing will be better understood with reference to the following examples. These examples are for the purpose of illustration. They are not to be considered limiting as to scope and nature of the present invention.

EXAMPLE I

Preparation of Primary Sertoli Cell-Enriched Culture Medium

Sertoli cell-enriched cultures were prepared from 20-day-old Sprague-Dawley rats using procedures of Mather & Sato (1979) with minor modifications as detailed elsewhere (Cheng et al., 1986; Cheng and Bardin, 1987). Sertoli cell aggregates of 5-10 cells recovered from enzymatic treatments using collagenase/dispase (Cheng et al., 1986) were filtered through a 102 $\mu$m mesh monofilament nylon cloth (Nitex HC3-102), washed four times in the serum-free culture medium (F-12/DME, 1:1, v/v, supplemented with 1.2 gm/l sodium bicarbonate, 15 mM HEPES, and 20 mg/l gentamycin) at 800 g (5 min. each). Cells were plated in 100 mm plastic culture dishes at a density of about $4.5 \times 10^6$ cells per dish (9 ml each) in the serum-free medium supplemented with 10 µg/ml insulin, 5 µg/ml human transferring, 2.5 µg/ml epidermal growth factor, 5 µg/ml bacitracin, $2 \times 10^{-7}$M testosterone, and 300 µg/ml ovine FSH. Bacitracin was included in the culture media and used as a nonspecific protease inhibitor (Patty et al., '77; Simmons and Ritzmann, '89). The cells were maintained at 30° C. in a humidified culture chamber with 95% air and 5% $CO_2$. Spent media were collected on day 4 and fresh media were added and the cells were cultured for an addition 4 days. Thereafter, media were collected, pooled, and stored at −20° C. until used. Three hundred fifty (350) ml of primary Sertoli cell-enriched culture medium per culture using 20 rats at 20 days of age were routinely obtained. A batch of 6 liters of Sertoli cell-enriched primary cultures were processed for purification using procedures as previously described (Cheng and Bardin, 1986; 1987; Cheng et al., 1988). The concentration and equilibration of media were performed on a Millipore Minitan TM ultrafiltration unit equipped with eight Millitan TM plates with Mr cutoff at 10,000 (Cheng et, 1989). All procedures were performed at 4° C. unless otherwise specified. Sample was filtered through a 0.2 µm Nalgene filtering unit before use.

EXAMPLE II

Isolational LCS

Anion-Exchange HPLC. The procedures used for the preparative fractionation of primary Sertoli cell-enriched culture medium on a Mono Q HR 10/16 ($16 \times 100$ mm i.d.; particle size, 10 µm) were performed as previously described (Cheng and Bardin, 1986; 1987; Cheng et al., 1988, 1989; Cheng, 1990). Media that had equilibrated against solvent A (20 mM Tris, pH 7.4 at 22° C.) and concentrated to about 100 ml in the above step were pumped onto the preparative column at a flow rate of 5 ml/min and proteins were eluted using a linear salt gradient of 0–80% solvent B (20 mM Tris, pH 7.4 at 22° C. containing 600 mM NaCl) at a flow rate of 5 ml/min over a period of 120 min.

Eluents from the anion-exchange HPLC column and from columns used for subsequent HPLC purification were simultaneously monitored by UV absorbance at 280 nm and by diode array technology using a LKB Model 2140 Rapid Spectral Detector with a spectrum of wavelengths ranged between 190 and 370 nm and an integration time of 1 second. Data were acquired and processed, and a chromatogram was monitored using a personal computer equipped with a video graphics adaptor which was interfaced to the Rapid Spectral Detector. The use of the diode array technology to monitor the protein elution profile provides many valuable strategies for the subsequent purification of putative paracrine factors contained in the Sertoli cell-enriched culture media since proteins that absorb poorly or not at all at 280 nm are readily identified using this technique. Thus, the complexity of the protein mixtures in a given column fraction can be readily identified.

Following separation of the Sertoli cell proteins by HPLC, a total of 12 major protein peaks was observed. An aliquot from each fraction was then withdrawn and bioassayed using the procedure of EXAMPLE IV for LCS. The concentrations of testosterone contained in each assay well were determined by radioimmunoassay. Only the bioactivity under Peak I was collected, pooled, and processed for subsequent purification.

Gel Permeation HPLC. Preparative gel permeation HPLC was performed essentially as previously described (Cheng and Bardin, 1987; Cheng et al., 1988a; Cheng et al., 1988b; Cheng, 1990). Fractions containing biological activity that stimulated Leydig cell steroidogenesis were pooled, concentrated to about 2 ml using an Amicon Model 8010 ultrafiltration unit equipped with a YM-10 membrane with a Mr cutoff at 10,000 and equilibrated against PBS buffer (10 mM sodium phosphate, pH 6.8 at 22° C. containing 0.15M NaCl). Sample was loaded onto a BioSil TSK-250 size exclusion HPLC column ($21.5 \times 600$ mm i.d.) at a flow rate of 3 ml/min and proteins were eluted using PBS buffer and eluates were monitored by UV absorbance at 280 nm. A total of four major protein peaks were noted and the biological activity was checked using the procedure of EXAMPLE IV. The activity was located in fractions between peaks 2 and 3. These fractions were pooled, equilibrated against double distilled water using an Amicon ultrafiltration unit (Model 8010) equipped with an Amicon YM-10 membrane, and lyophilized.

C4 Reversed-phase HPLC. The Leydig cell stimulator contained in the lyophilized sample was re-suspended in 2 ml of solvent A [5% ACN (acetronitrile)/95% $H_2O$, 0.1% TFA (trifluoroacetic acid), v/v] and pumped onto a preparative Vydac C4 reversed-phase preparative HPLC column ($22 \times 250$ mm i.d., particle size, 10 µm) at a flow rate of 4 ml/min. Proteins were eluted using a linear gradient of 5–80% solvent B (95% ACN/5% $H_2O$, 0.1% TFA, v/v) over a period of 90 min. A total of 12 protein peaks was observed. An aliquot from each of these fractions was bioassayed for LCS according to the procedure of EXAMPLE IV. It was noted that the biological activity for LCS corresponded with the eluted protein peak 1 (FIG. 3C). Fractions under this peak were pooled and lyophilized.

Diphenyl Reversed-phase HPLC. Partially purified LCS obtained from the above step was re-suspended in 200 µl of solvent A (5% ACN/95% $H_2O$, 0.1% TFA, v/v) and loaded onto a Vydac diphenyl reversed-phase HPLC column ($4.6 \times 250$ mm i.d.; particle size, 5 µm). Proteins that bound onto the column were eluted using a linear gradient of 40–100% solvent B (95% ACN/5% $H_2$), 0.1% TFA, v/v) over a period of 120 min and a total of eight protein peaks were noted. The biological activity as determined using the procedure of EXAMPLE IV was located under protein peak 3. Fractions under this peak were pooled, lyophilized, and re-suspended in 200 ml of solvent A.

C18 Reversed-Phase HPLC. The partially purified LCS recovered from phenyl reversed-phase HPLC was re-suspended in 200 µl of solvent A and injected onto a Vydac C18 reversed-phase HPLC column ($4.6 \times 250$ mm i.d.; particle size, 5 µm). A linear gradient of 10–70% solvent B (95% ACN/5% $H_2O$, 0.1% TFA, v/v) over a period of 100 min at a flow rate of 1 ml/min was used to elute the bound proteins. A total of nine protein peaks were detected and the biological activity was identified under protein peak 4 using the procedure of EXAMPLE IV. Using the procedures outlined above, the inventors obtained purified protein from 6 liters of crude spent media which contained about 200 mg total protein, thus a fold of about 1940 and a recovery of about 1.4% biological activity were achieved.

EXAMPLE III

Preparation of Purified Leydig Cells

Leydig cells were isolated from testes using a modification of procedures as previously described (Lefevre et al., 1983; Simpson et al., 1987). A group of 10 Sprague-Dawley rats at 80 days of age was killed by asphyxiation. Testes were removed and placed in serum-free medium [Ham's F-12 nutrient mixture:Dulbecco's modified Eagles (DME), 1:1, v/v] supplemented with 1.2 g/liter sodium bicarbonate, 15 mM HEPES, and 20 mg/liter gentamycin. The organs were rinsed twice in this medium to remove blood clots and residual tissues. The testes were then decapsulated and incubated in F-12/DME medium supplemented with 0.05% collagenase-dispase/0.005% soybean trypsin inhibitor (w/v) in a total volume of 5 ml/testis in 50-ml conical culture tubes. The culture tubes were suspended in a reciprocating water bath at 35° C. and shaken at a speed of 80 oscillations/min for 20 min. The crude cell suspension was filtered twice through Rytex ® polyamide nylon fiber (mesh 3-60/45) (Tetko Inc.). Cells were washed twice in F-12/DME medium at 200 g for 7 min and re-suspended in the serum-free medium at a concentration of $50 \times 10^6$ cells/0.5 ml per gradient fractionation. A discontinuous Percoll (Pharmacia/LKB Biotechnology) gradient of 20 to 80% was prepared in a 15-ml Corning round bottom centrifuge tube using two stock solutions of A (Percoll:10X F-12/DME medium; 9:1, v/v) and B (F-12/DME medium). Thirteen solutions with increasing Percoll concentrations from 20 to 80% of solution A were prepared by mixing appropriate volumes of solutions A and B and layered carefully in the 15 ml disposable centrifuge tube with the highest concentration of Percoll at the bottom. Cells were layered carefully on the top layer of the discontinuous gradient of Percoll which was at 20% and centrifuged at 1000 g for 20 min at 22° C. A total of 12 visible bands of testicular cells were noted at each interface between two distinctive Percoll concentrations. The cell fraction from each Percoll gradient interface was removed carefully by pipetting, washed twice in F-12/DME medium and sedimented by centrifugation at 200 g for 10 min and re-suspended in F-12/DME medium supplemented with insulin (10 µg/ml) and transferring (5 µg/ml). Cell number was determined using a hemocytometer. Cell viability was determined by trypan blue dye exclusion and the authenticity of Leydig cells was determined by $3\beta$-hydroxysteroid dehydrogenase ($3\beta$-HSD) histochemistry as previously described (Wiebe, 1976; Steinberger et al., 1966; Browning et al., 1981). It was noted that Leydig cells of greater than 90% purity were obtained in layers between 8, 9 and 10 as verified by $3\beta$-hydroxysteroid dehydrogenase staining. We routinely obtained $5 \times 10^6$ purified Leydig cells per preparation using five adult rats. For bioassays, purified Leydig cells were diluted to 50,000 cells/ml of F-12/DME medium supplemented with insulin and transferring as described above.

EXAMPLE IV

Bioassay of the LCS

Leydig cells purified by Percoll gradient centrifugation described in Example III were plated in 24 multiwells culture dishes. Each culture well contained 50,000 purified Leydig cells suspended in 1 ml of F-12/DME serum-free medium. To locate the stimulatory activity, an aliquot of 1–50 µl was withdrawn from each column fraction or sample and was incubated with purified Leydig cells for 24 hours in a humidified incubator at 35° C. with 95% air-5% $CO_2$. Thereafter, an aliquot was withdrawn for testosterone and/or cAMP measurement by radioimmunoassays. Control experiments were performed in which purified Leydig cells were incubated with various doses of hCG (0.02–10 ng/ml) or without added hormones for 24 hours.

cAMP determination. For cAMP determination, the spent media were heated at 100° C. for 10 min at the end of the culture period to inactivate phosphodiesterase activity, centrifuged in an Eppendorf microcentrifuge at 4° C. for 10 min to remove any debris and stored at $-20°$ C. until they were assayed. The concentrations of cAMP were then estimated using radioimmunoassay kits obtained from Amersham (Arlington Heights, Ill.) using procedures as provided by the supplier.

Testosterone determination. For testosterone determination, an aliquot of the spent medium from each culture well was withdrawn and measured by radioimmunoassay using anti-testosterone-3-(0-carboxymethyl)-oxime-BSA (Accurate Chemical & Scientific Corp., Westbury, N.Y.) and [1,2,6,7-$^3$H]testosterone (New England Nuclear, S.A. 89 Ci/mmol). Anti-testosterone antibody was diluted 1:80 using 0.05M Tris, pH 8.0 at 22° C. and a total of 500 µl was added onto each assay tube which contained 100 µl of sample and 100 µl of [$^3$H]testosterone in a final assay volume of 700 µl per tube. The assay tubes were incubated at 37° C. for 1 hr, followed by a 15 min incubation at 4° C., and 200 µl of dextran-coated charcoal solution (0.5% charcoal, 0.05% dextran T-70, w/v, in 0.05M Tris, pH 8.0 at 22° C.) was added onto each tube to separate free and bound [$^3$H]testosterone. Radioactivity was determined using a LKB Model 1209 Rackbeta $\beta$-liquid scintillation counter at 28% counting efficiency. The minimal detectable dose was 1.5 pg/assay tube and 50% displacement of the bound radioactivity was at 20 pg testosterone. A dose-response curve of testosterone production using Percoll purified Leydig cells by highly purified Leydig cell stimulator (0.01–5 ng protein) was obtained which showed a maximal stimulation of 10-fold over basal testosterone level at 5 ng with a half-maximal stimulation at 0.6 ng of protein.

A laboratory standard of the LCS was established using a pool of Sertoli cell-enriched culture medium prepared from 20-day-old Sprague-Dawley rats in the presence of 300 ng/ml ovine FSH. Procedures for the preparation of Sertoli cell-enriched culture media are described in EXAMPLE I and detailed in Cheng et al., '86; Cheng et al., '87; Cheng et al. '89; and Cheng and Bardin, '86. A serial dose of this laboratory standard designated CYCSTD-1-0-1 was run in every bioassay in aliquots of 0.06, 0.12, 0.25, 0.5, 1, and 2 µl; half maximal stimulation was observed at 0.7 µl/well.

A set of positive controls was established using purified hCG at doses of 0.025, 0.05, 0.1, 0.25, 0.5, 1, 5, and 10 ng/ml; half maximal stimulation was noted at 0.08 ng/ml and the maximal stimulation was at 1 ng/ml (FIG. 2B).

Negative controls were prepared using buffers from each HPLC purification step utilized for the purification of this biological factor.

Using a batch of crude Sertoli cell-enriched culture medium (CYCSTD-1-0-1) and various doses of highly purified hCG, it was noted that 1.2 μl of CYCSTD-1-0-1 was equivalent to one unit of bioactivity. Bioassays had a coefficient of interassay variation of about 20%.

EXAMPLE V

Determination of the Effects of FSH on the Production of this LCS by Sertoli Cells Various doses of FSH ranging between 0–1,000 ng/ml were added to different dishes of Sertoli cell-enriched cultures prepared in accordance with the procedure of EXAMPLE I at day 0, and spent media were collected at day 4 for bioassay of Leydig cell stimulator in accordance with the procedures at Example IV. It was noted that the production of LCS was highly dependent on FSH. Specifically, Sertoli cells ($4.5 \times 10^6$ cells/9 ml dish) were cultured in the presence of various concentrations of FSH (0–1,000 ng/ml) for four days. Dishes were terminated and 100 ml of spent media were withdrawn and bioassayed for Leydig cell stimulator using $5 \times 10^4$ purified Leydig cells/well for 24 hr.

EXAMPLE VI

Structural Analysis

When the batch of purified material obtained in Example II was resolved by SDS-PAGE under reducing and non-reducing conditions on a 12.5% T SDS-polyacrylamide gel, only a single silver stained band was noted with an apparent Mr of 17,000 indicating that it has a single polypeptide chain. The protein concentration was quantified on silver stained SDS-polyacrylamide gel by densitometric scanning using silver stained BSA as a standard. Densitometric scanning was performed on a EC910 densitometer (E-C Apparatus Corp., Petersburg, Fla.) interfaced with a Hewlett-Packard (Model HP3394A) integrator at 600 nm as previously described (Silvestrini et al., 1989).

EXAMPLE VII

Testosterone Secretion by Immature Leydig Cells

With reference to FIG. 1, LCS was prepared according to the procedures described in EXAMPLE II from Sertoli cell-enriched culture media as described in EXAMPLE I. Leydig cells from immature animals were purified according to the procedures described in EXAMPLE III for adult Leydig cells. Maximal stimulatory doses of LH and LCS were used according to techniques for bioassay described in EXAMPLE IV. Testosterone secretion was measured after five hours of exposure to LH and to LCS. Both LH and LCS caused about a tenfold increase in testosterone secretion by immature Leydig cells (C=control).

EXAMPLE VIII cAMP Accumulation by Immature Leydig Cells

With reference to FIG. 2, the effect of LH and LCS on the intercellular cAMP accumulation was measured. The studies were conducted using Leydig cells from immature animals which were purified according to the procedure described in EXAMPLE III for adult Leydig cells. LCS was prepared according to the procedures described in EXAMPLE II from Sertoli cell enriched culture media as described in EXAMPLE I. Maximal stimulatory doses of LH and LCS were used according to the bioassay technique described in EXAMPLE IV. LH produced a greater than fourfold increase in cAMP accumulation in the Leydig cells. By contrast, LCS produced no significant increase in cAMP accumulation in Leydig cells.

EXAMPLE IX

Synergistic Effect on Immature Leydig Cells

With reference to FIG. 3, the effects of a maximal stimulatory dose of LH and LCS on testosterone secretion by immature Leydig cells was analyzed. LCS was purified by the procedure outlined in EXAMPLE II. Preparation of immature Leydig cells used the same procedure as used for mature Leydig cells in EXAMPLE III. The bioassay of LCS and LH was the same as that described in EXAMPLE IV. Both LH and LCS produced at least about a tenfold increase in testosterone secretion. However, the combination of a maximal dose of LCS and a maximal dose of LH produced synergistic increase in testosterone (about 35-fold).

The principles, preferred embodiments, and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

---

We claim:

1. A Leydig cell stimulator comprising:
   a polypeptide having a Mr of between about 17,000 and about 20,000 as determined by SDS-PAGE when measured under reducing and non-reducing conditions characterized by the ability to stimulate at least about a 200 percent increase in androgen secretion by Leydig cells as compared to said cells' basal androgen secretion level, said leydig cell stimulator being in substantially pure and isolated form.

2. The Leydig cell stimulator of claim 1 wherein said polypeptide has an amine-terminal region of the structure of SEQ ID NO. 1.

3. A pharmaceutically active composition useful for stimulating and enhancing the production of androgen in animals in need of such treatment comprising: a pharmaceutically acceptable carrier and a Leydig cell stimulator comprising a polypeptide having an Mr of between about 17,000 and about 20,000 as determined by SDS-PAGE when measured under reducing and non-reducing conditions characterized by the ability to stimulate at least about a 200 percent increase in androgen secretion by Leydig cells as compared to said cells' basal androgen secretion level, said Leydig cell stimulator provided in an amount effective to stimulate and enhance androgen production.

4. The pharmaceutical composition of claim 3 wherein said Leydig cell stimulator has an N-terminal region of the structure of SEQ.ID NO. 1.

5. The pharmaceutical composition of claim 4 wherein said Leydig cell stimulator is in the form of a pharmaceutically acceptable salt.

6. A pharmaceutically active composition useful for stimulating and enhancing the production of androgen in animals in need of such treatment comprising: a pharmaceutically acceptable carrier, a first amount of a Leydig cell stimulator polypeptide having a Mr of between about 17,000 and about 20,000 as determined by SDS-PAGE when measured under reducing and non-reducing conditions characterized by the ability to stimulate at least about a 200 percent increase in androgen secretion by Leydig cells as compared to said cells' basal androgen secretion level and LH/CG provided in a second amount, said first and said second amounts of Leydig cell stimulator and LH/CG being effective to stimulate androgen production by said Leydig cells greater than that resulting from the exposure of said Leydig cells to either said first amount of Leydig cell stimulator or said second amount of LH/CG.

7. The pharmaceutically active composition of claim 6, wherein said first and said second amounts are sufficient to stimulate androgen production by Leydig cells greater than or equal to that resulting from the exposure of said Leydig cells to either a maximal stimulatory dose of LH/CG or a maximal stimulatory dose of Leydig cell stimulator.

8. The pharmaceutical composition of claim 6 wherein said Leydig cell stimulator has an N-terminal region of the structure of SEQ.ID NO. 1.

9. The pharmaceutical composition of claim 6 wherein said Leydig cell stimulator and said LH/CG are present in a maximal dose.

10. A method of enhancing the production of a Leydig cell stimulator having a polypeptide which has an Mr of between about 17,000 and about 20,000 as determined by SDS-PAGE when measured under reducing and non-reducing conditions characterized by the ability to stimulate at least about a 200 percent increase in androgen secretion by Leydig cells as compared to said cells' basal androgen level, in vivo, comprising the step of: administering at least one compound selected from the group consisting of FSH, LCS, or a mixture of LCS and LH/CG, to an animal in need of such treatment, in amounts sufficient to enhance the production of said Leydig cell stimulator.

11. A host cell including non-native DNA capable of expressing a polypeptide having a Mr of between about 17,000 and about 20,000 as determined by SDS-PAGE when measured under reducing and non-reducing conditions characterized by the ability to stimulate at least about a 200 percent increase in androgen secretion by Leydig cells as compared to said cells' basal androgen secretion level.

12. A Leydig cell stimulator comprising: a polypeptide having a Mr of between about 17,000 and about 20,000 as determined by SDS-PAGE when measured under reducing and non-reducing conditions characterized by the ability to stimulate a greater level of androgen when administered with a maximal stimulatory dose of LH to Leydig cells than said Leydig cells could produce by the administration of LH to said Leydig cells along.

* * * * *

UNITED STATES PATENT AND TRADEMARK OFFICE
CERTIFICATE OF CORRECTION

PATENT NO. : 5,304,603

DATED : April 19, 1994

INVENTOR(S) : Cheng et al.

It is certified that error appears in the above-identified patent and that said Letters Patent is hereby corrected as shown below:

Title page, item [56], under OTHER PUBLICATIONS, line 3, "Purificaiton" should read --Purification--.
Column 5, line 29, "cells," should read --cells'--.
Column 7, line 10, "+" should read --+--.
Column 14, line 8, "Protocols in Molecular" should read --Protocols in Molecular--.
Column 19, line 1, after "thus a" insert --purification--.
Column 23, line 13, "leydig" should read --Leydig--.

Signed and Sealed this

Thirtieth Day of August, 1994

Attest:

BRUCE LEHMAN

Attesting Officer        Commissioner of Patents and Trademarks